United States Patent
Hu

(10) Patent No.: US 7,312,079 B1
(45) Date of Patent: Dec. 25, 2007

(54) VARIANTS OF FAM3C

(75) Inventor: Yi Hu, Spring, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 11/543,007

(22) Filed: Oct. 4, 2006

Related U.S. Application Data

(60) Provisional application No. 60/724,366, filed on Oct. 6, 2005.

(51) Int. Cl.
*C12P 21/02* (2006.01)

(52) U.S. Cl. ............... 435/325; 435/252.3; 435/320.1; 435/69.5; 536/23.2; 536/23.5

(58) Field of Classification Search ............... None
See application file for complete search history.

(56) References Cited

U.S. PATENT DOCUMENTS

| | | | |
|---|---|---|---|
| 4,215,051 A | 7/1980 | Schroeder et al. |
| 4,378,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,272,057 A | 12/1993 | Smulson et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,114,598 A | 9/2000 | Kucherlapati et al. |
| 6,150,584 A | 11/2000 | Kucherlapati et al. |
| 6,506,607 B1 | 1/2003 | Shyjan |

FOREIGN PATENT DOCUMENTS

| WO | WO 04/088324 A2 | 10/2004 |
|---|---|---|
| WO | WO 05/032328 A2 | 4/2005 |
| WO | WO 05/035762 A1 | 4/2005 |

OTHER PUBLICATIONS

Philipenko et al, 2004, "Genomic organization and expression analysis of the murine Fam3c", Gene 335:159-168.
Zhu et al, 2002, "Cloning, Expression, and Initial Characterization of a Novel Cytokine-like Gene Family", Genomics 80(2):144-150.

*Primary Examiner*—Lorraine M. Spector
*Assistant Examiner*—Elly-Gerald Stoica
(74) *Attorney, Agent, or Firm*—Lance K Ishimoto; Peter G Seferian

(57) ABSTRACT

Polynucleotide and polypeptide sequences that encode novel variant FAM3C proteins are disclosed that can be used in therapeutic, diagnostic, and pharmacogenomic applications.

4 Claims, No Drawings

VARIANTS OF FAM3C

The present application claims the benefit of U.S. Provisional Application Ser. No. 60/724,366, which was filed on Oct. 6, 2005, and is herein incorporated by reference in its entirety.

1.0 INTRODUCTION

The present invention relates to the discovery, identification, and characterization of polynucleotides encoding proteins that are novel variants of human FAM3C gene (aliases include GS3786; GS3876; predicted osteoblast protein; ILEI and DNA segment, Chr 6, Wayne State University 176, expressed). The invention encompasses the described polynucleotides, host cell expression systems, the encoded proteins, fusion proteins, polypeptides and peptides, antibodies to the encoded proteins and peptides, and genetically engineered animals that either lack or overexpress the disclosed polynucleotides, antagonists and agonists of the proteins, and other compounds that modulate the expression or activity of the proteins encoded by the disclosed polynucleotides, which can be used for diagnosis, drug screening, clinical trial monitoring, the treatment of FAM3C-related disorders.

2.0 BACKGROUND OF THE INVENTION

Human FAM3C has been previously assigned to a subfamily of proteins that are characterized as cytokines (Zhu, et al., 2002, Genomics 80:144-150). The term cytokine was used initially to separate a group of immunomodulatory proteins, from other growth factors that modulate the proliferation and bioactivities of non-immune cells. Cytokine is a generic name for a diverse group of soluble proteins and peptides which act as humoral regulators which, either under normal or pathological conditions, modulate the functional activities of individual cells and tissues. Many cytokines show stimulating or inhibitory activities and may synergise or antagonize also the actions of other factors. A single cytokine may elicit reactions also under certain circumstances which are the reverse of those shown under other circumstances.

However, information presented herein, suggests that FAM3C and the novel variants described in this application bear structural similarity to certain enzymes, particularly glycosyltransferases. The biological roles of glycans includes those that rely on the structural and modulatory properties of glycans and those that rely on specific recognition of glycan structures by other molecules (generally receptor proteins or lectins). The second group can be divided into those involving recognition by endogenous receptors within the same organism and those resulting from recognition by exogenous agents, such as but not limited to, pathogen receptors and toxins.

3.0 SUMMARY OF THE INVENTION

The present invention relates to the discovery, identification, and characterization of nucleotides that encode novel variants of human FAM3C, and the corresponding amino acid sequences of these proteins. The sequence of the novel variants of FAM3C protein described in this application are also present in mice and chimpanzees. The invention also encompasses agonists and antagonists of the described transporter proteins, including small molecules, large molecules, mutant variant FAM3C proteins, or portions thereof, that compete with native variant FAM3C proteins, peptides, and antibodies, as well as nucleotide sequences that can be used to inhibit the expression of the described variant FAM3C proteins (e.g., antisense and ribozyme molecules, and open reading frame or regulatory sequence replacement constructs) or to enhance the expression of the described variant FAM3C proteins (e.g., expression constructs that place the described polynucleotide under the control of a strong promoter system), and transgenic animals that express a transporter protein sequence, or "knock-outs" (which can be conditional) that do not express a functional transporter protein. Knock-out mice can be produced in several ways, one of which involves the use of mouse embryonic stem cell ("ES cell") lines that contain gene trap mutations in a murine homolog of at least one of the described human transporter sequences.

When the unique FAMC3 protein sequences described in SEQ ID NOS:1-16 are "knocked-out" they provide a method of identifying phenotypic expression of the particular gene, as well as a method of assigning function to previously unknown genes. In addition, animals in which the unique transporter sequences described in SEQ ID NOS:1-16 are "knocked-out" provide an unique source in which to elicit antibodies to homologous and orthologous proteins, which would have been previously viewed by the immune system as "self" and therefore would have failed to elicit significant antibody responses. To these ends, gene trapped knockout ES cells have been generated using murine homologs of certain of the described variant FAM3C proteins.

Additionally, the unique transporter encoding sequences described in SEQ ID NOS:1-16 are useful for the identification of protein coding sequences, and mapping an unique gene to a particular chromosome. These sequences identify biologically verified exon splice junctions, as opposed to splice junctions that may have been bioinformatically predicted from genomic sequence alone. The sequences of the present invention are also useful as additional DNA markers for restriction fragment length polymorphism (RFLP) analysis, in population biology and in forensic biology, particularly given the presence of nucleotide polymorphisms within the described sequences.

Further, the present invention also relates to processes for identifying compounds that modulate, i.e., act as agonists or antagonists of, FAMC3 protein expression and/or FAMC3 protein activity, that utilize purified preparations of the described variant FAM3C proteins and/or FAMC3 protein gene products, or cells expressing the same. Such compounds can be used as therapeutic agents for the treatment of any of a wide variety of symptoms associated with FAM3C-related disorders.

4.0 BRIEF DESCRIPTION OF THE SEQUENCE LISTING

The Sequence Listing provides the known sequence of human FAM3C and novel variants thereof. These human FAM3C polynucleotide sequences (SEQ ID NOS: 1, 3, 5, 7, 9, 11, 13 and 15) and deduced amino acid sequences (SEQ ID NOS: 2, 4, 6, 8, 10, 12, 14 and 16) of the described proteins are presented in the Sequence Listing.

5.0 DETAILED DESCRIPTION OF THE INVENTION

The present invention relates to the discovery, identification and characterization of novel variants of the mammalian FAM3C gene (aliases include GS3786; GS3876; predicted osteoblast protein; ILEI and DNA segment, Chr 6, Wayne State University 176, expressed). The human FAM3C gene (GENBANK Accession Nos: NM_014888, NP_055703 and Q92520, among others) is present on human chromosome 7. The mouse (*Mus musculus*) ortholog of the human FAM3C gene, also known as D6Wsu176e (DNA segment, Chr 6, Wayne State University 176, expressed) is located on chromosome 6 (6 A3.1; 6 2.0 cM; GENBANK Accession Nos. AAH44170 and AY424275). Additional animal orthologs include for example, but are not limited to, the rat (*Rattus norvegicus*, NP_942066 and AY228475) and zebrafish (*Danio rerio*, AAH66710, NM_212725, BC044170.1 and BC066710.1).

A U.S. patent and several patent applications have also been published that describe the sequence, and partial forms thereof, and prophetic utility of FAM3C including U.S. Pat. No. 6,506,607, US2002155438, and US2003073623, the disclosures of which are each incorporated by reference in their entirety.

In addition, recently published P.C.T. Application No. WO2005035762 and related European Application Nos. EP04009790 and EP03019551, describe the activity of a cytokine-like protein designated ILEI (Interleukin-Like Epithelial-mesenchymal transition (EMT) Inducer). This protein is the same as FAM3C (Accession Nos: NM_014888 and Q92520). ILEI was identified on the basis of its upregulation on the level of polysome-bound RNA and on the level of secreted protein after Ras/TGFβ-induced epithelial to mesenchymal transition in the murine mammary gland cell system. Overexpression of ILEI (FAM3C) was found to induce EMT in non-tumorigenic mammary epithelial cells (EpH4) and to render these cells tumorigenic in nude mice. Further, in related EpRasC40 cells, which have a Ras mutation and are tumorigenic in nude mice but do not normally induce EMT or metastasize, the addition of partially purified recombinant ILEI (FAM3C) protein or the stable overexpression of ILEI (FAM3C) in EpRasC40 cells resulted in increased tumor growth and lung metastasises, along with enhanced cell motility and migration in respective assays. Based on these findings, it was stated that modulation of ILEI (FAM3C) activity has utility in the prevention and treatment of cancer and the therapy of fibrotic diseases and chronic obstructive pulmonary disease.

Furthermore, published P.C.T. Application No. WO2004088324 and (related U.S. Application No. US2004008954) identifies, among others, a FAM3C precursor as a protein present in amniotic fluid and refers to their use in determining the state of maternal/fetal conditions and P.C.T. Application No. WO2005032328 A2 (and related U.S. Application No. US2004015761) refers to the use of a group of proteins, including FAM3C, in the identification, prevention and therapy of rheumatoid arthritis.

Zhu, et al., 2002 (Genomics 80: 144-150) identified FAMC3, by searching a database for sequences similar to FAM3A, followed by RT-PCR of heart mRNA to clone FAM3C. The deduced 227-amino acid protein contains an N-terminal signal peptide. The authors predicted that FAM3C is a secreted cytokine protein that forms a 4-helix bundle, and 3-dimensional modeling indicated that 4 cysteines could form 2 disulfide bonds linking helices 1 and 4 and helices 2 and 3. Northern blot analysis detected FAM3C expression in almost all tissues tested.

FAM3C has also been identified by some as a candidate gene for autosomal recessive nonsyndromic hearing loss locus 17 (DFNB17). In the mouse FAM3C was found to be ubiquitously expressed in all analyzed tissues, and had two major transcript variants presumed to result from an alternative use of two distinct polyadenylation signals. Additionally, analyses of putative amino acid sequences of FAM3C orthologous proteins showed that their primary and secondary structures and overall topology were highly conserved. Various programs for bioinformatic analysis of FAM3C sequences suggest a potential N-terminus membrane spanning region, a predicted transmembrane domain between amino acids 9 and 27, a predicted cytoplasmic domain between amino acids 1 and 8, and some have predicted a signal peptide between amino acids 1-24. Similar topology and secondary structure were predicted for human (GenBank accession no: D87120), mouse (GenBank accession no: BC009086), rat (GenBank accession no: AY228475) and zebrafish (GenBank accession no: BC044170), with a greater than 90% similarity between human, rat and mice and 60% similarity between the mammal and the zebrafish (Pilipenko V V, et al., 2004. Gene 335:159-68). These authors also noted that FAM3C shares a common domain with, among others, O-linked mannose beta 1,2-N-acetylglucosaminyltransferase (GnT I.2), which has been hypothesised to be involved in signaling in mammals during embryogenesis. However the authors discount these similarities by stating that the alignment occurs at an inactive site of GnT I.2 and that this suggests that these proteins do not have acetylglucosaminyltransferase activity. Further, they note that because the expression pattern of mouse FAM3C resembles the known pattern of the Nkx5 homeobox genes and analysis of the FAM3C promoter region demonstrated a putative Nkx5.1 binding site, they hypothesize that FAM3C may be a downstream target gene for the Nkx5.1 transcription factor, and may thus be involved in cell differentiation and proliferation during inner ear embryogenesis.

While not being committed to any particular mechanism, applicants note that FAM3C was assigned to a subfamily of proteins that have been bioinformatically characterized as cytokines. However, advanced comparative linear sequence and structural alignments suggest that FAM3C also bears structural similarity to certain glycosyltransferases and may have glycosyltransferase activity. Accordingly, certain embodiments of the present invention relate to treatment of a FAM3C related disorder by administering a therapeutically effective amount of a glycosyltransferase.

While not being committed to any one particular mechanism, applicants note that several lines of evidence indicate that FAM3C may be a glycosyltransferase. Unlike most secreted ligands FAM3C proteins from different organisms are highly conserved. For example, the entire FAM3C molecule is conserved among divergent animals (93-100% identity); while the well known secreted protein erythropoietin is only 78% identical between mouse and human.

In addition, nonlinear analysis of FAM3C (independent of sequence order) demonstrates that FAM3C is more closely related to enzymes than to known secreted ligands. Blast local alignment studies show that homology exists between FAM3C and GnT I.2, which is a glycosyltransferase. What others have characterized as a putative signal peptide of FAM3C, is more likely a type II transmembrane domain which is conserved among glycosyltransferases. Phylogenetic studies place FAM3C close to several glycosyltransferase subfamilies and FAM3C also shares modules (submotifs) with glycosyltransferases.

Furthermore, secondary structure predictions of FAM3C conform to the general arrangement observed with glycosyltransferases (i.e., sets of anti-parallel beta sheets separating alpha helices, all intermixed with coiled coils) and 3D structure predictions of FAM3C conform generally with those of glycosyltransferase structures: an N-terminal transmembrane anchor, a small stem that contains a convertase cleavage site, followed by a globular region. Many glycosyltransferases are golgi enzymes, and have an N-terminus similar to that of FAM3C (type II transmembrane), a short "stem," and then the enzymatically active portion that resides in the Golgi. This perhaps indicates that FAM3C is a transmembrane enzyme that is targeted to the golgi via its N-terminus. In the golgi, as a glycosyltransferase, FAM3C could modify fucosyl residue by adding additional sugars to it. By way of example, but not limitation, modification of fucose residues (by FRINGE-type glycosyltransferases) regulate NOTCH responses to ligands and subsequent signaling that activates gene transcription. Depending upon the state of glycosylation, NOTCH can activate genes or suppress gene expression in response to various ligands. Thus, NOTCH itself has regulatory activity over, for example, certain aspects of actin biology and cytoskeletal formation. Therefore, such a mechanism is not without biological precedence.

Accordingly, certain embodiments of the present invention relate to treatment of a FAM3C related disorder by administering a therapeutically effective amount of a glycosyltransferase, glycotransferase stimulator or inhibitor. Glycosyltransferases are well studied and well known to those of skill in the art, (see, for example, the techniques described in "Essentials of Glycobiology", 1999, Varki, A., et al. eds., Cold Spring Harbor Laboratory Press, NY; "Techniques in Glycobiology", 1997, Townsend, R. R. and Hotchkiss, A. T., Jr. eds. CRC Press, Marcel Dekker, NY; "Guide to Techniques in Glycobiology (Methods in Enzymology)", 1994, Abelson, J, N., et al., eds. Academic Press, NY; "Functional and Molecular Glycobiology (Bios Series Advanced Texts)", 2002, Brooks S. A, Dwek, M. V. and Schumacher, U., BIOS Scientific Publishers each of which is incorporated by reference herein in its entirety) as are activators and inhibitors (see for example, Laferte et al., 2000, Eur J Biochem 267:4840; Hu et al., 2004, Chem & Bio 11:703).

The present invention encompasses the nucleotides presented in the Sequence Listing, host cells expressing such nucleotides, the expression products of such nucleotides, and: (a) nucleotides that encode mammalian homologs of the described polynucleotides, including the specifically described variant FAM3C proteins, and the FAMC3 protein products; (b) nucleotides that encode one or more portions of the described variant FAM3C proteins and that correspond to functional domains, and the polypeptide products specified by such nucleotide sequences, including, but not limited to, the novel regions of any active domain(s); (c) isolated nucleotides that encode mutant versions, engineered or naturally occurring, of the described variant FAM3C proteins in which all or a part of at least one domain is deleted or altered, and the polypeptide products specified by such nucleotide sequences, including, but not limited to, soluble proteins and peptides in which all or a portion of the signal (or one or more hydrophobic transmembrane) sequence is deleted; (d) nucleotides that encode chimeric fusion proteins containing all or a portion of a coding region of a FAMC3 protein, or one of its domains (e.g., a receptor or ligand binding domain, accessory protein/self-association domain, etc.) fused to another peptide or polypeptide; or (e) therapeutic or diagnostic derivatives of the described polynucleotides, such as oligonucleotides, antisense polynucleotides, ribozymes, dsRNA, siRNA, or gene therapy constructs comprising a sequence first disclosed in the Sequence Listing.

As discussed above, the present invention includes the human DNA sequences presented in the Sequence Listing (and vectors comprising the same), and additionally contemplates any nucleotide sequence encoding a contiguous human FAMC3 protein open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., N.Y., at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent FAMC3 product. Functional equivalents of a FAMC3 protein include naturally occurring variant FAM3C proteins present in other species, and mutant variant FAM3C proteins, whether naturally occurring or engineered (by site directed mutagenesis, gene shuffling, directed evolution as described in, for example, U.S. Pat. No. 5,837,458). The invention also includes degenerate nucleic acid variants of the disclosed FAMC3 polynucleotide sequences.

Additionally contemplated are polynucleotides encoding FAMC3 ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package, as described herein, using standard default settings).

The invention also includes nucleic acid molecules, preferably DNA molecules, that hybridize to, and are therefore the complements of, the described FAMC3 nucleotide sequences or alternate splice variants thereof. Such hybridization conditions may be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such FAMC3 oligonucleotides can be used as hybridization probes for screening libraries, and assessing gene expression patterns (particularly using a microarray or high-throughput "chip" format). Additionally, a series of FAMC3 oligonucleotide sequences, or the complements thereof, can be used to represent all or a portion of the described FAMC3 sequences. An oligonucleotide or polynucleotide sequence first disclosed in at least a portion of one or more of the sequences of SEQ ID NOS:1-16 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1-16, or an amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445, 934, 5,252,743, 4,713,326, 5,424,186, and 4,689,405, the disclosures of which are herein incorporated by reference in their entirety.

Addressable arrays comprising sequences first disclosed in SEQ ID NOS:1-16 can be used to identify and characterize the temporal and tissue specific expression of a gene. These addressable arrays incorporate oligonucleotide sequences of sufficient length to confer the required specificity, yet they must be within the limitations of the production technology. The length of these probes is usually within a range of between about 8 to about 2000 nucleotides. Preferably, the probes consist of 60 nucleotides, and more preferably 25 nucleotides, from the sequences first disclosed in SEQ ID NOS:1-16.

For example, a series of the described FAMC3 oligonucleotide sequences, or the complements thereof, can be used in chip format to represent all or a portion of the described sequences. The oligonucleotides, typically between about 16 to about 40 (or any whole number within the stated range) nucleotides in length, can partially overlap each other, and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing, and proceed in either a sense (5'-to-3') orientation vis-a-vis the described sequence or in an antisense orientation.

Microarray-based analysis allows the discovery of broad patterns of genetic activity, providing new understanding of gene functions, and generating novel and unexpected insight into transcriptional processes and biological mechanisms. The use of addressable arrays comprising sequences first disclosed in SEQ ID NOS:1-16 provides detailed information about transcriptional changes involved in a specific pathway, potentially leading to the identification of novel components, or gene functions that manifest themselves as novel phenotypes.

Probes consisting of sequences first disclosed in SEQ ID NOS:1-16 can also be used in the identification, selection, and validation of novel molecular targets for drug discovery. The use of these unique sequences permits the direct confirmation of drug targets, and recognition of drug dependent changes in gene expression that are modulated through pathways distinct from the intended target of the drug. These unique sequences therefore also have utility in defining and monitoring both drug action and toxicity.

As an example of utility, the sequences first disclosed in SEQ ID NOS:1-16 can be utilized in microarrays, or other assay formats, to screen collections of genetic material from patients who have a particular medical condition. These investigations can also be carried out using the sequences first disclosed in SEQ ID NOS:1-16 in silico, and by comparing previously collected genetic databases and the disclosed sequences using computer software known to those in the art.

Thus, the sequences first disclosed in SEQ ID NOS:1-16 can be used to identify mutations associated with a particular FAM3C-related disorder.

FAM3C preparations (for example, but not limited to, cells expressing FAM3C, FAMC3 proteins, peptides, alternative splice variants or fragments thereof) or FAM3C-antagonists (e.g., antibodies, other molecules that interfere with FAM3C's activity or molecules that retard or inhibit the functional expression of FAM3C such as FAM3C antisense or small inhibitory RNA molecules) present opportunities for therapeutic intervention in treating a wide variety of conditions that have been linked to FAMC3.

Diseases and disorders associated with human variant FAM3C proteins include, but are not limited to, seizures, mental illness, dementia, diabetes, Alzheimer's disease, depression, kidney disease, digestive/bowel disorders, high blood pressure, cardiopulmonary disease, fibrotic diseases and chronic obstructive pulmonary disease, infectious disease, immune mediated, autoimmune and inflammatory disorders (such as, but not limited to, NK cell mediated disease, systemic lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive 35 enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft—versus-host-disease), engraftment of hematopoietic progenitor cells, bone marrow transplantation related disorders, neoangiogeneis, bone disease, wound healing, vascular proliferation, various pathologic maternal/fetal conditions (such as intra-amniotic infection, or chromosomal defects), autoimmune diseases, thrombocytopenia, (such as, but not limited to, drug induced thrombocytopenia, idiopathic thrombocytopenic purpura, thrombotic thrombocytopenic purpura, post-transfusion purpura, hemolytic-uremic syndrome, disseminated intravascular coagulation, malignant hypertension, eclampsia, vasculitis associated with systemic autoimmune disorders), thrombosis, myocardial infarction and acute cardiac syndrome, arrhythmia, cancers (such as, but not limited to, cancers of the bladder, kidney, prostate, breast, colon, ovary and pancreas, leukemia, acute lymphoblastic leukemia and secondary acute myeloid leukemia), obesity, connective tissue disorders and infertility (collectively FAM3C-related disorders). Accordingly, the described novel splice variants of human FAM3C protein can be useful in detecting and treating such conditions.

Given the similar information and expression data, the described human FAMC3s can be targeted (by drugs, oligos, antibodies, etc.) in order to treat disease, or to therapeutically augment the efficacy of, for example, chemotherapeutic agents used in the treatment of FAM3C-related disorders.

In addition to small molecule inhibitors of FAM3C expression and/or activity, the invention also contemplates the use of large molecules to effect the level, activity, or bioavailability of FAMC3 in vivo, including, but not limited to, mutant FAMC3 proteins or peptides that compete with native FAMC3, anti-FAMC3 antibodies, and nucleotide sequences that can be used to inhibit (reduce or eliminate) FAMC3 gene expression (including, but not limited to, small interfering RNA (siRNA), small hairpin RNA (shRNA), antisense, ribozyme, and/or triplex molecules, and coding or regulatory sequence replacement constructs). In certain embodiments of the present invention, such compounds, or pharmaceutical compositions comprising one or more such compounds, can be used as prophylactic or therapeutic agents for the prevention or treatment of FAMC3 related disorders, or any of a wide variety of symptoms or conditions associated with FAMC3 related disorders. The present invention further provides compositions comprising one or more such compounds for use in treating or preventing FAMC3 related disorders or related diseases, disorders, or conditions. Use of such compounds in the manufacture of a medicament for treating or preventing FAMC3 related disorders is also contemplated. The present invention also encompasses compositions comprising a biologically or therapeutically effective amount of one or more of such compounds for use in the preparation of a medicament for use in prevention and/or treatment of FAMC3 related disorders.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence, in conjunction with the presence of one or more specific oligonucleotide sequence(s) first disclosed in SEQ ID NOS: 1-16. Alternatively, a restriction map specifying the relative positions of restriction endonuclease digestion sites, or various palindromic or other specific oligonucleotide sequences, can be used to structurally describe a given sequence. Such restriction maps, which are typically generated by widely available computer programs (e.g., the University of Wisconsin GCG sequence analysis package, SEQUENCER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as FAMC3 antisense molecules useful, for example, in FAMC3 protein gene regulation and/or as antisense primers in amplification reactions of FAMC3 nucleic acid sequences. With respect to FAMC3 protein gene regulation, such techniques can be used to regulate biological functions. Further, such sequences may be used as part of ribozyme and/or triple helix sequences that are also useful for FAMC3 protein gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine) 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330). Alternatively, double stranded RNA can be used to disrupt the expression and function of a targeted FAMC3.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448-7451), etc.

Low stringency conditions are well-known to those of skill in the art, and will vary predictably depending on the specific organisms from which the library and the labeled sequences are derived. For guidance regarding such conditions, see, for example, Sambrook et al., 1989, Molecular Cloning, A Laboratory Manual, Cold Spring Harbor Press, Cold Spring Harbor, N.Y. (and periodic updates thereof), and Ausubel et al., 1989, supra.

Alternatively, suitably labeled FAMC3 nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a FAMC3 protein gene homolog can be isolated from nucleic acid from an organism of interest by performing PCR using two degenerate or "wobble" oligonucleotide primer pools designed on the basis of amino acid sequences within the FAMC3 protein products disclosed herein. The template for the reaction may be genomic DNA, or total RNA, mRNA, and/or cDNA obtained by reverse transcription of mRNA prepared from human or non-human cell lines or tissue known to express, or suspected of expressing, an allele of a FAMC3 protein gene.

The PCR product can be subcloned and sequenced to ensure that the amplified sequences represent the sequence of the desired FAMC3 protein gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, a FAMC3 protein gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see, e.g., Sambrook et al., 1989, supra.

A cDNA encoding a mutant FAMC3 protein sequence can be isolated, for example, by using PCR. In this case, the first cDNA strand may be synthesized by hybridizing an oligo-dT oligonucleotide to mRNA isolated from tissue known to express, or suspected of expressing, a FAMC3 protein, in an individual putatively carrying a mutant FAMC3 protein allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant FAMC3 protein allele to that of a corresponding normal FAMC3 protein allele, the mutation(s) responsible for the loss or alteration of function of the mutant FAMC3 protein gene product can be ascertained.

Alternatively, a genomic library can be constructed using DNA obtained from an individual suspected of carrying, or known to carry, a mutant FAMC3 protein allele (e.g., a person manifesting a FAMC3 protein-associated phenotype such as, for example, obesity, high blood pressure, connective tissue disorders, infertility, etc.), or a cDNA library can be constructed using RNA from a tissue known to express, or suspected of expressing, a mutant FAMC3 protein allele. A normal FAMC3 protein gene, or any suitable fragment thereof, can then be labeled and used as a probe to identify the corresponding mutant FAMC3 protein allele in such libraries. Clones containing mutant FAMC3 sequences can then be purified and subjected to sequence analysis according to methods well-known to those skilled in the art.

Additionally, an expression library can be constructed utilizing cDNA synthesized from, for example, RNA isolated from a tissue known to express, or suspected of expressing, a mutant FAMC3 protein allele in an individual suspected of carrying, or known to carry, such a mutant allele. In this manner, gene products made by the putatively mutant tissue can be expressed and screened using standard antibody screening techniques in conjunction with antibodies raised against a normal FAMC3 protein product, as described below (for screening techniques, see, for example, Harlow and Lane, eds., 1988, "Antibodies: A Laboratory Manual", Cold Spring Harbor Press, Cold Spring Harbor, N.Y.).

Additionally, screening can be accomplished by screening with labeled FAMC3 protein fusion proteins, such as, for example, alkaline phosphatase-FAMC3 protein or FAMC3 protein-alkaline phosphatase fusion proteins. In cases where a FAMC3 protein mutation results in an expression product with altered function (e.g., as a result of a missense or a frameshift mutation), polyclonal antibodies to a FAMC3 protein are likely to cross-react with a corresponding mutant FAMC3 protein expression product. Library clones detected via their reaction with such labeled antibodies can be purified and subjected to sequence analysis according to methods well-known in the art.

The present invention thus includes the use of nucleotide sequences that encode mutant isoforms of any of the FAM3C amino acid sequences, peptide fragments thereof, truncated versions thereof, and/or fusion proteins including any of the above fused to another unrelated polypeptide. Examples of such polypeptides can include, but are not limited to, an epitope tag that aids in purification or detection of the resulting fusion protein, or an enzyme, fluorescent protein, or luminescent protein that can be used as a marker.

FAM3C nucleic acid molecules may also encode or act as antisense molecules, useful, for example, in FAM3C gene regulation, and/or as antisense primers in amplification reactions of FAM3C nucleic acid sequences. With respect to FAM3C gene regulation, such techniques can be used to regulate one or more of the biological functions associated with FAM3C, as described herein. Further, such sequences can be used as part of ribozyme and/or triple helix sequences that are also useful for FAM3C gene regulation. Such antisense nucleic acids can also encompass an RNA molecule that reduces expression of a target nucleic acid by an RNA interference (RNAi)-based mechanism. Certain exemplary RNA molecules suitable for RNAi include, but are not limited to, short interfering RNA (siRNAs), short hairpin RNA (shRNAs), microRNA, tiny non-coding RNA (tncRNA), and small modulatory RNA (smRNA) molecules (see, e.g., Novina and Sharp, Nature 430:161-164, 2004).

In certain aspects of the present invention, the inhibitory antisense or double stranded oligonucleotides comprise at least one modified base moiety that is selected from the group including, but not limited to, 5-fluorouracil, 5-chlorouracil, 5-bromouracil, 5-iodouracil, hypoxanthine, xanthine, 5-(carboxyhydroxylmethyl) uracil, dihydrouracil, 5-methoxyuracil, 5-carboxymethylaminomethyl-2-thiouridine, 5-carboxymethylaminomethyluracil, 5-methoxyaminomethyl-2-thiouracil, 5-methyl-2-thiouracil, 5-methyluracil, 2-thiouracil, 4-thiouracil, pseudouracil, uracil-5-oxyacetic acid (v), uracil-5-oxyacetic acid methylester, 3-(3-amino-3-N-2-carboxypropyl) uracil, 5-methylaminomethyluracil, 5'-methoxycarboxymethyluracil, inosine, 1-methylinosine, N6-adenine, N6-isopentenyladenine, 2-methyladenine, 2-methylthio-N6-isopentenyladenine, queosine, beta-D-galactosylqueosine, beta-D-mannosylqueosine, 1-methylguanine, 2-methylguanine, 7-methylguanine, 2,2-dimethylguanine, 3-methylcytosine, 5-methylcytosine, 4-acetylcytosine, 2-thiocytosine, wybutoxosine, (acp3)w, and 2,6-diaminopurine.

In certain embodiments of the present invention, the antisense oligonucleotides comprise at least one modified sugar moiety selected from the group including, but not limited to, arabinose, 2-fluoroarabinose, xylulose, and hexose. In other embodiments of the present invention, the antisense oligonucleotides comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof. In yet other embodiments of the present invention, the antisense oligonucleotides are α-anomeric oligonucleotides. An α-anomeric oligonucleotide forms specific double-stranded hybrids with complementary RNA in which, contrary to the usual β-units, the strands run parallel to each other (Gautier et al., Nucl. Acids Res. 15:6625-6641, 1987). The oligonucleotide can also be a 2'-0-methylribonucleotide
(Inoue et al., Nucl. Acids Res. 15:6131-6148, 1987), or a chimeric RNA-DNA analogue (Inoue et al., FEBS Lett. 215:327-330, 1987). Alternatively, double stranded RNA can be used to disrupt the expression and function of FAM3C.

The activity of an antisense nucleic acid, such as an antisense DNA or siRNA molecule, is often affected by the secondary structure of the target mRNA (see, e.g., Vickers et al., J. Biol. Chem. 278:7108-7118, 2003). Thus, an antisense nucleic acid can be selected that is complementary to a region of a target mRNA that is available for base-pairing. A suitable region of a target mRNA can be identified by performing a "gene walk", e.g., by empirically testing a number of antisense oligonucleotides for their ability to hybridize to various regions along a target mRNA and/or to reduce target mRNA expression (see, e.g., Vickers et al., supra, and Hill et al., Am. J. Respir. Cell Mol. Biol. 21:728-737, 1999). Alternatively, a suitable region of a target mRNA can be identified using an mRNA secondary structure prediction program or related algorithm to identify regions of a target mRNA that do not hybridize to any other regions of the target mRNA (see, e.g., Hill et al., supra). A combination of the above methods can also be used to identify a suitable region of a target mRNA. Several software systems exist to compute siRNA sequences, these include but are not limited to, siDirect, HuSiDa, siRNAdb siSearch, SpecificityServer and miRacle.

The invention also encompasses: (a) DNA vectors that contain any of the foregoing FAMC3 protein coding sequences and/or their complements (i.e., antisense); (b) DNA expression vectors that contain any of the foregoing FAMC3 protein coding sequences operatively associated with a regulatory element that directs the expression of the coding sequences (for example, baculovirus as described in U.S. Pat. No. 5,869,336, herein incorporated by reference); (c) genetically engineered host cells that contain any of the foregoing FAMC3 coding sequences operatively associated with a regulatory element that directs the expression of the coding sequences in the host cell; and (d) genetically engineered host cells that express an endogenous FAMC3 protein sequence under the control of an exogenously introduced regulatory element (i.e., gene activation). As used herein, regulatory elements include, but are not limited to, inducible and non-inducible promoters, enhancers, operators, and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 or adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a FAMC3 protein, as well as compounds or nucleotide constructs that inhibit expression of a FAMC3 protein sequence (transcription factor inhibitors, antisense and ribozyme molecules, or open reading frame sequence or regulatory sequence replacement constructs), or promote the expression of a FAMC3 protein (e.g., expression constructs in which FAMC3 protein coding sequences are operatively associated with expression control elements such as promoters, promoter/enhancers, etc.).

The variant FAM3C proteins or FAMC3 peptides, FAMC3 fusion proteins, FAMC3 nucleotide sequences, antibodies, antagonists and agonists can be useful for the detection of mutant variant FAM3C proteins, or inappropriately expressed variant FAM3C proteins, for the diagnosis of FAM3C-related disorders. The variant FAM3C proteins or peptides, FAMC3 fusion proteins, FAMC3 nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a FAMC3 protein in the body. The use of engineered host cells and/or animals may offer an advantage in that such systems allow not only for the identification of compounds that bind to the endogenous receptor for a FAMC3 protein, but can also identify compounds that trigger FAMC3 protein-mediated activities or pathways.

Finally, the FAMC3 protein products can be used as therapeutics. For example, soluble derivatives such as FAMC3 protein peptides/domains corresponding to variant FAM3C proteins, FAMC3 fusion protein products (especially FAMC3 protein-Ig fusion proteins, i.e., fusions of a FAMC3 protein, or a domain of a FAMC3 protein, to an IgFc), FAMC3 protein antibodies and anti-idiotypic antibodies (including Fab fragments), antagonists or agonists (including compounds that modulate or act on downstream targets in a FAMC3 protein-mediated pathway) can be used to directly treat FAM3C-related disorders. For instance, the administration of an effective amount of a soluble FAMC3 protein, a FAMC3 protein-IgFc fusion protein, or an anti-idiotypic antibody (or its Fab) that mimics the FAMC3 protein, could activate or effectively antagonize an endogenous FAMC3 protein activity. Nucleotide constructs encoding such FAMC3 protein products can be used to genetically engineer host cells to express such products in vivo; these genetically engineered cells function as "bioreactors" in the body delivering a continuous supply of FAMC3 protein, FAMC3 peptide, or FAMC3 fusion protein to the body. Nucleotide constructs encoding functional variant FAM3C proteins, mutant variant FAM3C proteins, as well as antisense and ribozyme molecules, can also be used in "gene therapy" approaches for the modulation of FAMC3 expression. Thus, the invention also encompasses pharmaceutical formulations and methods for treating FAM3C-related disorders.

Various aspects of the invention are described in greater detail in the subsections below.

7.1 THE HUMAN FAMC3 SEQUENCES

The cDNA sequences and the corresponding deduced amino acid sequences of the described variant FAM3C proteins (SEQ ID NOS:1-16) and the known sequence of human FAM3C are presented in the Sequence Listing. The expected coding region of the nucleic acid sequence encoding human FAM3C is 684 nucleotides in length (including the stop codon, GENBANK Accession No: NM_014888) and encodes a protein of 227 amino acids in length (GENBANK Accession No: Q92520). Both the expected and novel variant sequences of human FAM3C were obtained from human lymph node cDNA libraries (CLONTECH, Palo Alto, Calif.).

SEQ ID NO:1 encodes a novel longer variant of human FAM3C and variants thereof that result from point mutations that result in amino acid alterations. This novel variant contains a additional 51 base pair exon that encodes an additional 17 amino acids to the protein (SEQ ID NO:2). This exon is present in the published human genomic sequence and in that of the chimpanzee, however it appears to be absent from the published genome of the mouse and of others animals (dog, chicken, etc.). This additional exon also appears in an intron-less pseudogene in which an Alu sequence interrupts the FAM3C sequence on the X chromosome of the human genome. This intron-less pseudogene could give rise to a novel fusion transcript (nucleic acid 1 through 650).

In contrast, SEQ ID NO: 3 encodes a novel shorter variant of human FAM3C that has a 51 base pair deletion within the open reading frame of the expected FAM3C nucleic acid sequence that results in a 17 amino acid deletion from the expected FAM3C amino acid sequence. This deletion begins at amino acid 110 of the expected amino acid of FAM3C sequence (GENBANK Accession No: Q92520) and runs to amino acid position 127. This deletion results in a protein that is 210 amino acids in length as opposed to the expected length of 227 amino acids.

Several of the variants contain one or more nucleic acid polymorphisms that result in amino acid alterations and some are also contain nucleic acid polymorphisms that are silent. SEQ ID NO: 5 encodes a protein of the expected 227 amino acids but it contains an A/G polymorphism at the nucleotide position 368 of SEQ ID NO:5, which results in a Asp to Gly change at the region corresponding to amino acid position 123 of SEQ ID NO:6.

SEQ ID NO: 7 also encodes a protein of the expected 227 amino acids but it too contains a T/C polymorphism at the nucleotide position 386 of SEQ ID NO:7, which results in a Val to Ala change at the region corresponding to amino acid position 129 of SEQ ID NO:8.

SEQ ID NO: 9 also encodes a protein of the expected 227 amino acids but it too contains a T/C polymorphism at the nucleotide position 394 of SEQ ID NO: 9, which results in a Phe to Leu change at the region corresponding to amino acid position 132 of SEQ ID NO:10.

SEQ ID NO: 11 also encodes a protein of the expected 227 amino acids but it contains several polymorphisms, an A/G polymorphism at nucleotide position 268 of SEQ ID NO: 11, results in a Asn to Asp change at the region corresponding to amino acid position 90 of SEQ ID NO: 12. There is also a T/C polymorphism at nucleotide position 386 of SEQ ID NO: 11, that results in a Val to Ala change at the region corresponding to amino acid position 129 of SEQ ID NO: 12. Finally, there is also a A/G polymorphism at nucleotide position 420 of SEQ ID NO: 11 that is silent and does not result in an amino acid change in SEQ ID NO: 12.

SEQ ID NO: 13 also encodes a protein of the expected 227 amino acids but it contains several polymorphisms, a T/C polymorphism at nucleotide position 44 of SEQ ID NO: 13, results in a Val to Ala change at the region corresponding to amino acid position 15 of SEQ ID NO: 14. There is also a A/G polymorphism at nucleotide position 368 of SEQ ID NO: 13, that results in a Asp to Gly change at the region corresponding to amino acid position 123 of SEQ ID NO: 14.

SEQ ID NO: 15 also encodes a protein of the expected 227 amino acids but it contains several polymorphisms, a A/C polymorphism at nucleotide position 370 of SEQ ID NO: 15, results in a Met to Leu change at the region corresponding to amino acid position 124 of SEQ ID NO: 16. There is also a T/C polymorphism at nucleotide position 585 of SEQ ID NO: 15 that is silent and does not result in an amino acid change in SEQ ID NO: 16.

These polymorphisms in the sequences of the present invention have utility in forensic analysis and in population biology, for example in establishing human or humanoid migration patterns. The very presence of the longer novel splice variant sequence or protein (SEQ ID NOS:1 or 2, respectively) would likely identify a tissue sample as human or humanoid in origin. While it could also indicate that the tissue were possibly from a chimpanzee, since chimpanzees, unlike humans, have not grown to populate them globe, the effects of this alternative conclusion would be quite limited.

Expression of FAM3C splice variants, as determined using RT-PCR and primers to the novel human FAM3C variant with the additional exon (51 nt), showed expression in, inter alia, human cerebellum, adrenal gland, salivary gland, heart, bladder, eye, osteosarcoma, embryonic carcinoma, spinal cord, eye, fetal kidney, fetal lung, tongue, embryo 6 weeks old, adenocarcinoma, osteosarcoma cell-lines and microvascular endothelial cell-lines.

The described human FAM3C protein is apparently encoded on human chromosome 7(see GENBANK Accession Nos: NM_014888, NP_055703 and Q92520, among others). Accordingly, the described sequences are useful for mapping coding regions of human genomic sequence as well as identifying and biologically validating exon splice junctions. This is particularly true since the novel variant of FAM3C is itself the product of alternative splicing. An additional application of the described novel human polynucleotide sequences is their use in the molecular mutagenesis/evolution of proteins that are at least partially encoded by the described novel sequences using, for example, polynucleotide shuffling or related methodologies (see, e.g., U.S. Pat. Nos. 5,830,721 and 5,837,458).

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

FAMC3 protein gene products can also be expressed in transgenic animals. Animals of any species, except humans, including, but not limited to, worms, mice, rats, rabbits, guinea pigs, pigs, micro-pigs, birds, goats, and non-human primates, e.g., baboons, monkeys, and chimpanzees, may be used to generate FAMC3 protein transgenic animals.

Any technique known in the art may be used to introduce a FAMC3 protein transgene into animals to produce the founder lines of transgenic animals. Such techniques include, but are not limited to, pronuclear microinjection (Hoppe and Wagner, 1989, U.S. Pat. No. 4,873,191); retrovirus-mediated gene transfer into germ lines (Van der Putten et al., 1985, Proc. Natl. Acad. Sci. USA 82:6148-6152); gene targeting in embryonic stem cells (Thompson et al., 1989, Cell 56:313-321); electroporation of embryos (Lo, 1983, Mol. Cell. Biol. 3:1803-1814); and sperm-mediated gene transfer (Lavitrano et al., 1989, Cell 57:717-723); etc. For a review of such techniques, see Gordon, 1989, Transgenic Animals, Intl. Rev. Cytol. 115:171-229, which is incorporated by reference herein in its entirety.

The present invention provides for transgenic animals that carry a FAMC3 protein transgene in all their cells, as well as animals that carry a transgene in some, but not all of their cells, i.e., mosaic animals or somatic cell transgenic animals. A transgene may be integrated as a single transgene, or in concatamers, e.g., head-to-head tandems or head-to-tail tandems. A transgene may also be selectively introduced into and activated in a particular cell-type by following, for example, the teaching of Lasko et al., 1992, Proc. Natl. Acad. Sci. USA 89:6232-6236. The regulatory sequences required for such a cell-type specific activation will depend upon the particular cell-type of interest, and will be apparent to those of skill in the art.

When it is desired that a FAMC3 protein transgene be integrated into the chromosomal site of the endogenous FAMC3 protein gene, gene targeting is preferred. Briefly, when such a technique is to be utilized, vectors containing some nucleotide sequences homologous to the endogenous FAMC3 protein gene are designed for the purpose of integrating, via homologous recombination with chromosomal sequences, into and disrupting the function of the nucleotide sequence of the endogenous FAMC3 protein gene (i.e., "knockout" animals).

The transgene can also be selectively introduced into a particular cell-type, thus inactivating the endogenous FAMC3 protein gene in only that cell-type, by following, for example, the teaching of Gu et al., 1994, Science 265:103-106. The regulatory sequences required for such a cell-type specific inactivation will depend upon the particular cell-type of interest, and will be apparent to those of skill in the art.

Once transgenic animals have been generated, the expression of the recombinant FAMC3 protein gene may be assayed utilizing standard techniques. Initial screening may be accomplished by Southern blot analysis or using PCR techniques to analyze animal tissue to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of FAMC3 protein gene-expressing tissue may also be evaluated immunocytochemically using antibodies specific for the FAMC3 protein transgene product.

The present invention also provides for "knock-in" animals. Knock-in animals are those in which a polynucleotide sequence (i.e., a gene or a cDNA) that the animal does not naturally have in its genome is inserted in such a way that it is expressed. Examples include, but are not limited to, a human gene or cDNA used to replace its murine ortholog in the mouse, a murine cDNA used to replace the murine gene in the mouse, and a human gene or cDNA or murine cDNA that is tagged with a reporter construct used to replace the murine ortholog or gene in the mouse. Such replacements can occur at the locus of the murine ortholog or gene, or at another specific site. Such knock-in animals are useful for the in vivo study, testing and validation of, intra alia, human drug targets, as well as for compounds that are directed at the same, and therapeutic proteins.

7.2 VARIANT HUMAN FAM3C PROTEINS AND POLYPEPTIDES

Variant FAM3C proteins, FAMC3 polypeptides, FAMC3 peptide fragments, mutated, truncated, or deleted forms of the variant FAM3C proteins, and/or FAMC3 fusion proteins can be prepared for a variety of uses. These uses include, but are not limited to, the generation of antibodies, as reagents in diagnostic assays, for the identification of other cellular gene products related to a FAMC3 protein, and as reagents in assays for screening for compounds that can be used as pharmaceutical reagents useful in the therapeutic treatment of FAM3C-related disorders. Given the similar information and expression data, the described variant FAM3C proteins can be targeted (by drugs, oligos, antibodies, etc.) in order to treat FAM3C-related disorders, or to therapeutically augment the efficacy of, for example, chemotherapeutic agents used in the treatment of cancer.

The Sequence Listing discloses the amino acid sequences encoded by the described FAMC3 polynucleotides. The variant FAM3C proteins typically display initiator methionines in DNA sequence contexts consistent with a translation initiation site. Many of the sequences described display signal type sequences similar to those often found on membrane proteins; however, all of the described proteins display multiple transmembrane hydrophobic domains typical of membrane associated proteins.

The described FAMC3 amino acid sequences of the present invention include the amino acid sequences presented in the Sequence Listing, as well as analogues and derivatives thereof. Further, corresponding FAMC3 protein homologues from other species are encompassed by the invention. In fact, any FAMC3 protein encoded by the FAMC3 nucleotide sequences described herein are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al., eds., Scientific American Books, New York, N.Y., herein incorporated by reference), are generically representative of all the various permutations and combinations of nucleic acid sequences that can encode such amino acid sequences.

The invention also encompasses proteins that are functionally equivalent to the variant FAM3C proteins encoded by the presently described nucleotide sequences, as judged by any of a number of criteria, including, but not limited to, the ability to transport a substrate of the novel variant FAM3C proteins described, the ability to effect an identical or complementary downstream pathway, or a change in cellular metabolism (e.g., proteolytic activity, ion flux, tyrosine phosphorylation, etc.). Such functionally equivalent variant FAM3C proteins include, but are not limited to, additions or substitutions of amino acid residues within the amino acid sequence encoded by the FAM3C nucleotide sequences described herein, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the FAMC3 nucleotide sequences of the invention. Where, as in the present instance, the FAMC3 peptide or polypeptide is thought to be from a membrane protein, the hydrophobic regions of the protein can be excised, and the resulting soluble peptide or polypeptide can be recovered from the culture media. Such expression systems also encompass engineered host cells that express a FAMC3 protein, or functional equivalent, in situ. Purification or enrichment of a FAMC3 protein from such expression systems can be accomplished using appropriate detergents and lipid micelles and methods well-known to those skilled in the art. However, such engineered host cells themselves may be used in situations where it is important not only to retain the structural and functional characteristics of a FAMC3 protein, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing FAMC3 nucleotide sequences; yeast (e.g., *Saccharomyces, Pichia*) transformed with recombinant yeast expression vectors containing FAMC3 nucleotide sequences; insect cell systems infected with recombinant virus expression vectors (e.g., baculovirus) containing FAMC3 nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing FAMC3 nucleotide sequences; or mammalian cell systems (e.g., COS, CHO, BHK, 293, 3T3) harboring recombinant expression constructs containing FAMC3 nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the FAMC3 protein product being expressed. For example, when a large quantity of such a protein is to be produced for the generation of pharmaceutical compositions of, or containing, a FAMC3 protein, or for raising antibodies to a FAMC3 protein, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a FAMC3 protein coding sequence may be ligated individually into the vector in-frame with the lacZ coding region so that a fusion protein is produced; pIN vectors (Inouye and Inouye, 1985, Nucleic Acids Res. 13:3101-3109; Van Heeke and Schuster, 1989, J. Biol. Chem. 264:5503-5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads, followed by elution in the presence of free glutathione. The PGEX vectors are designed to include thrombin or factor Xa protease cleavage sites so that the cloned target expression product can be released from the GST moiety.

In an exemplary insect system, *Autographa californica* nuclear polyhedrosis virus (AcNPV) is used as a vector to express foreign polynucleotide sequences. The virus grows in *Spodoptera frugiperda* cells. A FAMC3 protein coding sequence can be cloned individually into a non-essential region (for example the polyhedrin gene) of the virus and placed under control of an AcNPV promoter (for example the polyhedrin promoter). Successful insertion of a FAMC3 protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the FAMC3 nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a FAMC3 protein product in infected hosts (e.g., see Logan and Shenk, 1984, Proc. Natl. Acad. Sci. USA 81:3655-3659). Specific initiation signals may also be required for efficient translation of inserted FAMC3 nucleotide sequences. These signals include the ATG initiation codon and adjacent sequences. In cases where an entire FAMC3 protein gene or cDNA, including its own initiation codon and adjacent sequences, is inserted into the appropriate expression vector, no additional translational control signals may be needed. However, in cases where only a portion of a FAMC3 protein coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516-544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the desired modification and processing of the foreign protein expressed. To this end, eukaryotic host cells that possess the cellular machinery for the desired processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the FAMC3 protein sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express a FAMC3 protein product. Such engineered cell lines may be particularly useful in screening and evaluation of compounds that affect the endogenous activity of a FAMC3 protein product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. Another exemplary system allows for the ready purification of non-denatured fusion proteins expressed in human cell lines (Janknecht et al., 1991, Proc. Natl. Acad. Sci. USA 88:8972-8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns, and histidine-tagged proteins are selectively eluted with imidazole-containing buffers.

Also encompassed by the present invention are fusion proteins that direct a FAMC3 protein to a target organ and/or facilitate transport across the membrane into the cytosol. Conjugation of variant FAM3C proteins to antibody molecules or their Fab fragments could be used to target cells bearing a particular epitope. Attaching an appropriate signal sequence to a FAMC3 protein would also transport a FAMC3 protein to a desired location within the cell. Alternatively, targeting of a FAMC3 protein or its nucleic acid sequence might be achieved using liposome or lipid complex based delivery systems. Such technologies are described in "Liposomes: A Practical Approach", New, R.R. C., ed., Oxford University Press, N.Y., and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of variant FAM3C proteins to a target site or desired organ, where they cross the cell membrane and/or the nucleus where the variant FAM3C proteins can exert their functional activity. This goal may be achieved by coupling of a FAMC3 protein to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences), to facilitate passage across cellular membranes, and can optionally be engineered to include nuclear localization signals.

Additionally contemplated are oligopeptides that are modeled on an amino acid sequence first described in the Sequence Listing. Such FAMC3 protein oligopeptides are generally between about 10 to about 100 amino acids long, or between about 16 to about 80 amino acids long, or between about 20 to about 35 amino acids long, or any variation or combination of sizes represented therein that incorporate a contiguous region of sequence first disclosed in the Sequence Listing. Such FAMC3 protein oligopeptides can be of any length disclosed within the above ranges, and can initiate at any amino acid position represented in the Sequence Listing.

The invention also contemplates "substantially isolated" or "substantially pure" proteins or polypeptides. The phrase "substantially isolated" or "substantially pure" protein or polypeptide is meant to describe a protein or polypeptide that has been separated from at least some of those components that naturally accompany it. Typically, the protein or polypeptide is substantially isolated or pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially isolated or pure protein or polypeptide may be obtained, for example, by extraction from a natural source, by expression of a recombinant nucleic acid encoding the protein or polypeptide, or by chemically synthesizing the protein or polypeptide.

Purity can be measured by any appropriate method, e.g., column chromatography such as immunoaffinity chromatography using an antibody specific for the protein or polypeptide, polyacrylamide gel electrophoresis, or HPLC analysis. A protein or polypeptide is substantially free of naturally associated components when it is separated from at least some of those contaminants that accompany it in its natural state. Thus, a polypeptide that is chemically synthesized or produced in a cellular system different from the cell from which it naturally originates will be, by definition, substantially free from its naturally associated components. Accordingly, substantially isolated or pure proteins or polypeptides include eukaryotic proteins synthesized in *E. coli*, other prokaryotes, or any other organism in which they do not naturally occur.

7.3 ANTIBODIES TO HUMAN FAMC3 PROTEIN PRODUCTS

Antibodies that specifically recognize one or more epitopes of a FAMC3 protein, epitopes of conserved variants of a FAMC3 protein, or peptide fragments of a FAMC3 protein, are also encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of a FAMC3 protein in a biological sample and may, therefore, be utilized as part of a diagnostic or prognostic technique whereby patients may be tested for abnormal amounts of a FAMC3 protein. Such antibodies may also be utilized in conjunction with, for example, compound screening schemes for the evaluation of the effect of test compounds on expression and/or activity of a FAMC3 protein expression product. Additionally, such antibodies can be used in conjunction with gene therapy to, for example, evaluate normal and/or engineered FAMC3 protein-expressing cells prior to their introduction into a patient. Such antibodies may additionally be used in methods for the inhibition of abnormal FAMC3 protein activity. Thus, such antibodies may be utilized as a part of treatment methods.

For the production of antibodies, various host animals may be immunized by injection with a FAMC3 protein, a FAMC3 peptide (e.g., one corresponding to a functional domain of a FAMC3 protein), a truncated FAMC3 protein polypeptide (a FAMC3 protein in which one or more domains have been deleted), functional equivalents of a FAMC3 protein or mutated variants of a FAMC3 protein. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and/or coupling with molecules such as keyhole limpet hemocyanin, tetanus toxoid, diphtheria toxoid, ovalbumin, cholera toxin, or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class, including IgG, IgM, IgE, IgA, and IgD, and any subclass thereof. The hybridomas producing the mabs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,114,598, 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 341:544-546) can be adapted to produce single chain antibodies against FAMC3 protein expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')$_2$ fragments, which can be produced by pepsin digestion of an antibody molecule; and Fab fragments, which can be generated by reducing the disulfide bridges of F(ab')$_2$ fragments. Alternatively, Fab expression libraries may be constructed (Huse et al., 1989, Science, 246:1275-1281) to allow rapid and easy identification of monoclonal Fab fragments with the desired specificity.

Antibodies to a FAMC3 protein can, in turn, be utilized to generate anti-idiotype antibodies that "mimic" a given FAMC3 protein, using techniques well-known to those skilled in the art (see, e.g., Greenspan and Bona, 1993, FASEB J. 7:437-444; and Nissinoff, 1991, J. Immunol. 147:2429-2438). For example, antibodies that bind to a FAMC3 protein domain and competitively inhibit the binding of a FAMC3 protein to its cognate receptor can be used to generate anti-idiotypes that "mimic" the FAMC3 protein and, therefore, bind and activate or neutralize a receptor. Such anti-idiotypic antibodies, or Fab fragments of such anti-idiotypes, can be used in therapeutic regimens involving a FAMC3 protein-mediated pathway. Additionally, given the high degree of relatedness of mammalian variant FAM3C proteins, the presently described knock-out mice (having never seen a FAMC3 protein, and thus never been tolerized to a FAMC3 protein) have an unique utility, as they can be advantageously applied to the generation of antibodies against the disclosed mammalian variant FAM3C proteins (i.e., a FAMC3 protein will be immunogenic in FAMC3 protein knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All cited publications, patents, and patent applications are herein incorporated by reference in their entirety with the exception of any teaching that directly conflicts with the superceding disclosure presented herein.

What is claimed is:

1. An isolated nucleic acid molecule that encodes the amino acid sequence of SEQ ID: 2 or 4.

2. The isolated nucleic acid molecule of claim 1, wherein said nucleic acid molecule comprises the nucleotide sequence of SEQ ID NO:1 or 3.

3. An expression vector comprising the isolated nucleic acid molecule of claim 1.

4. A host cell comprising the expression vector of claim 3.

* * * * *

SEQUENCE LISTING

<160> NUMBER OF SEQ ID NOS: 16

<210> SEQ ID NO 1
<211> LENGTH: 735
<212> TYPE: DNA
<213> ORGANISM: Homo Sapiens
<220> FEATURE:
<221> NAME/KEY: CDS
<222> LOCATION: (1)...(735)

<400> SEQUENCE: 1

```
atg agg gta gca ggt gct gca aag ttg gtg gta gct gtg gca gtg ttt         48
Met Arg Val Ala Gly Ala Ala Lys Leu Val Val Ala Val Ala Val Phe
 1               5                  10                  15 tta ctg aca ttt tat gtt att tct caa gta ttt gaa ata aaa atg gat         96
Leu Leu Thr Phe Tyr Val Ile Ser Gln Val Phe Glu Ile Lys Met Asp
             20                  25                  30 gca agt tta gga aat cta ttt gca aga tca gca ttg gac aca gct gca        144
Ala Ser Leu Gly Asn Leu Phe Ala Arg Ser Ala Leu Asp Thr Ala Ala
         35                  40                  45 cgt tct aca aag cct ccc aga tat aag tgt ggg atc tca aaa gct tgc        192
Arg Ser Thr Lys Pro Pro Arg Tyr Lys Cys Gly Ile Ser Lys Ala Cys
     50                  55                  60 cct gag aag cat ttt gct ttt aaa atg gca agt gga gca gcc aac gtg        240
Pro Glu Lys His Phe Ala Phe Lys Met Ala Ser Gly Ala Ala Asn Val
 65                  70                  75                  80 gtg gga ccc aaa atc tgc ctg gaa gat aat gtt tta atg agt ggt gtt        288
Val Gly Pro Lys Ile Cys Leu Glu Asp Asn Val Leu Met Ser Gly Val
                 85                  90                  95 aag aat aat gtt gga aga ggg atc aat gtt gcc ttg gca aat gga aaa        336
Lys Asn Asn Val Gly Arg Gly Ile Asn Val Ala Leu Ala Asn Gly Lys
            100                 105                 110 aca gga gaa gta tta gac act aaa tat ttt gac atg tgg gga gga gcc        384
Thr Gly Glu Val Leu Asp Thr Lys Tyr Phe Asp Met Trp Gly Gly Ala
        115                 120                 125 cca gga ata tca ata cga aag aca cag gat aaa tca gga atg gga aat        432
Pro Gly Ile Ser Ile Arg Lys Thr Gln Asp Lys Ser Gly Met Gly Asn
    130                 135                 140 tat gtg gca cca ttt att gag ttt ctg aag gcc ata caa gat gga aca        480
Tyr Val Ala Pro Phe Ile Glu Phe Leu Lys Ala Ile Gln Asp Gly Thr
145                 150                 155                 160 ata gtt tta atg gga aca tac gat gat gga gca acc aaa ctc aat gat        528
Ile Val Leu Met Gly Thr Tyr Asp Asp Gly Ala Thr Lys Leu Asn Asp
                165                 170                 175 gag gca cgg cgg ctc att gct gat ttg ggg agc aca tct att act aat        576
Glu Ala Arg Arg Leu Ile Ala Asp Leu Gly Ser Thr Ser Ile Thr Asn
            180                 185                 190 ctt ggt ttt aga gac aac tgg gtc ttc tgt ggt ggg aag ggc att aag        624
Leu Gly Phe Arg Asp Asn Trp Val Phe Cys Gly Gly Lys Gly Ile Lys
```

```
Leu Gly Phe Arg Asp Asn Trp Val Phe Cys Gly Gly Lys Gly Ile Lys
        195                 200                 205 aca aaa agc cct ttt gaa cag cac ata aag aac aat aag gat aca aac      672
Thr Lys Ser Pro Phe Glu Gln His Ile Lys Asn Asn Lys Asp Thr Asn
        210                 215                 220 aaa tat gaa gga tgg cct gaa gtt gta gaa atg gaa gga tgc atc ccc      720
Lys Tyr Glu Gly Trp Pro Glu Val Val Glu Met Glu Gly Cys Ile Pro
225                 230                 235                 240 cag aag caa gac taa                                                  735
Gln Lys Gln Asp  *
```

<210> SEQ ID NO 2
<211> LENGTH: 244
<212> TYPE: PRT
<213> ORGANISM: Homo Sapiens

<400> SEQUENCE: 2

```
Met Arg Val Ala Gly Ala Ala Lys Leu Val Val Ala Val Ala Val Phe
 1               5                  10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Met Trp Gly Gly Ala
        115                 120                 125

Pro Gly Ile Ser Ile Arg Lys Thr Gln Asp Lys Ser Gly Met Gly Asn
    130                 135                 140

Tyr Val Ala Pro Phe Ile Glu Phe Leu Lys Ala Ile Gln Asp Gly Thr
145                 150                 155                 160

Ile Val Leu Met Gly Thr Tyr Asp Asp Gly Ala Thr Lys Leu Asn Asp
                165                 170                 175

Glu Ala Arg Arg Leu Ile Ala Asp Leu Gly Ser Thr Ser Ile Thr Asn
            180                 185                 190

Leu Gly Phe Arg Asp Asn Trp Val Phe Cys Gly Gly Lys Gly Ile Lys
        195                 200                 205

Thr Lys Ser Pro Phe Glu Gln His Ile Lys Asn Asn Lys Asp Thr Asn
    210                 215                 220

Lys Tyr Glu Gly Trp Pro Glu Val Val Glu Met Glu Gly Cys Ile Pro
225                 230                 235                 240

Gln Lys Gln Asp
```

<210> SEQ ID NO 3
<211> LENGTH: 633
<212> TYPE: DNA
<213> ORGANISM: Homo Sapiens
<220> FEATURE:
<221> NAME/KEY: CDS
<222> LOCATION: (1)...(633)

<400> SEQUENCE: 3

```
atg agg gta gca ggt gct gca aag ttg gtg gta gct gtg gca gtg ttt      48
Met Arg Val Ala Gly Ala Ala Lys Leu Val Val Ala Val Ala Val Phe
 1               5                  10                  15 tta ctg aca ttt tat gtt att tct caa gta ttt gaa ata aaa atg gat      96
Leu Leu Thr Phe Tyr Val Ile Ser Gln Val Phe Glu Ile Lys Met Asp
             20                  25                  30 gca agt tta gga aat cta ttt gca aga tca gca ttg gac aca gct gca    144
Ala Ser Leu Gly Asn Leu Phe Ala Arg Ser Ala Leu Asp Thr Ala Ala
         35                  40                  45 cgt tct aca aag cct ccc aga tat aag tgt ggg atc tca aaa gct tgc    192
Arg Ser Thr Lys Pro Pro Arg Tyr Lys Cys Gly Ile Ser Lys Ala Cys
 50                  55                  60 cct gag aag cat ttt gct ttt aaa atg gca agt gga gca gcc aac gtg    240
Pro Glu Lys His Phe Ala Phe Lys Met Ala Ser Gly Ala Ala Asn Val
 65                  70                  75                  80 gtg gga ccc aaa atc tgc ctg gaa gat aat gtt tta atg agt ggt gtt    288
Val Gly Pro Lys Ile Cys Leu Glu Asp Asn Val Leu Met Ser Gly Val
                 85                  90                  95 aag aat aat gtt gga aga ggg atc aat gtt gcc ttg gca aat gat gtg    336
Lys Asn Asn Val Gly Arg Gly Ile Asn Val Ala Leu Ala Asn Asp Val
            100                 105                 110 gca cca ttt att gag ttt ctg aag gcc ata caa gat gga aca ata gtt    384
Ala Pro Phe Ile Glu Phe Leu Lys Ala Ile Gln Asp Gly Thr Ile Val
        115                 120                 125 tta atg gga aca tac gat gat gga gca acc aaa ctc aat gat gag gca    432
Leu Met Gly Thr Tyr Asp Asp Gly Ala Thr Lys Leu Asn Asp Glu Ala
    130                 135                 140 cgg cgg ctc att gct gat ttg ggg agc aca tct att act aat ctt ggt    480
Arg Arg Leu Ile Ala Asp Leu Gly Ser Thr Ser Ile Thr Asn Leu Gly
145                 150                 155                 160 ttt aga gac aac tgg gtc ttc tgt ggt ggg aag ggc att aag aca aaa    528
Phe Arg Asp Asn Trp Val Phe Cys Gly Gly Lys Gly Ile Lys Thr Lys
                165                 170                 175 agc cct ttt gaa cag cac ata aag aac aat aag gat aca aac aaa tat    576
Ser Pro Phe Glu Gln His Ile Lys Asn Asn Lys Asp Thr Asn Lys Tyr
            180                 185                 190 gaa gga tgg cct gaa gtt gta gaa atg gaa gga tgc atc ccc cag aag    624
Glu Gly Trp Pro Glu Val Val Glu Met Glu Gly Cys Ile Pro Gln Lys
        195                 200                 205 caa gac taa                                                         633
Gln Asp  *
    210

<210> SEQ ID NO 4
<211> LENGTH: 210
<212> TYPE: PRT
<213> ORGANISM: Homo Sapiens

<400> SEQUENCE: 4

Met Arg Val Ala Gly Ala Ala Lys Leu Val Val Ala Val Ala Val Phe
 1               5                  10                  15

Leu Leu Thr Phe Tyr Val Ile Ser Gln Val Phe Glu Ile Lys Met Asp
             20                  25                  30

Ala Ser Leu Gly Asn Leu Phe Ala Arg Ser Ala Leu Asp Thr Ala Ala
         35                  40                  45

Arg Ser Thr Lys Pro Pro Arg Tyr Lys Cys Gly Ile Ser Lys Ala Cys
 50                  55                  60

Pro Glu Lys His Phe Ala Phe Lys Met Ala Ser Gly Ala Ala Asn Val
 65                  70                  75                  80
```

```
Val Gly Pro Lys Ile Cys Leu Glu Asp Asn Val Leu Met Ser Gly Val
            85                  90                  95

Lys Asn Asn Val Gly Arg Gly Ile Asn Val Ala Leu Ala Asn Asp Val
            100                 105                 110

Ala Pro Phe Ile Glu Phe Leu Lys Ala Ile Gln Asp Gly Thr Ile Val
            115                 120                 125

Leu Met Gly Thr Tyr Asp Asp Gly Ala Thr Lys Leu Asn Asp Glu Ala
            130                 135                 140

Arg Arg Leu Ile Ala Asp Leu Gly Ser Thr Ser Ile Thr Asn Leu Gly
145                 150                 155                 160

Phe Arg Asp Asn Trp Val Phe Cys Gly Gly Lys Gly Ile Lys Thr Lys
                    165                 170                 175

Ser Pro Phe Glu Gln His Ile Lys Asn Lys Asp Thr Asn Lys Tyr
            180                 185                 190

Glu Gly Trp Pro Glu Val Val Glu Met Glu Gly Cys Ile Pro Gln Lys
            195                 200                 205

Gln Asp
    210

<210> SEQ ID NO 5
<211> LENGTH: 684
<212> TYPE: DNA
<213> ORGANISM: Homo Sapiens
<220> FEATURE:
<221> NAME/KEY: CDS
<222> LOCATION: (1)...(684)

<400> SEQUENCE: 5 atg agg gta gca ggt gct gca aag ttg gtg gta gct gtg gca gtg ttt      48
Met Arg Val Ala Gly Ala Ala Lys Leu Val Val Ala Val Ala Val Phe
  1               5                  10                  15 tta ctg aca ttt tat gtt att tct caa gta ttt gaa ata aaa atg gat     96
Leu Leu Thr Phe Tyr Val Ile Ser Gln Val Phe Glu Ile Lys Met Asp
                20                  25                  30 gca agt tta gga aat cta ttt gca aga tca gca ttg gac aca gct gca    144
Ala Ser Leu Gly Asn Leu Phe Ala Arg Ser Ala Leu Asp Thr Ala Ala
            35                  40                  45 cgt tct aca aag cct ccc aga tat aag tgt ggg atc tca aaa gct tgc    192
Arg Ser Thr Lys Pro Pro Arg Tyr Lys Cys Gly Ile Ser Lys Ala Cys
        50                  55                  60 cct gag aag cat ttt gct ttt aaa atg gca agt gga gca gcc aac gtg    240
Pro Glu Lys His Phe Ala Phe Lys Met Ala Ser Gly Ala Ala Asn Val
 65                  70                  75                  80 gtg gga ccc aaa atc tgc ctg gaa gat aat gtt tta atg agt ggt gtt    288
Val Gly Pro Lys Ile Cys Leu Glu Asp Asn Val Leu Met Ser Gly Val
                    85                  90                  95 aag aat aat gtt gga aga ggg atc aat gtt gcc ttg gca aat gga aaa    336
Lys Asn Asn Val Gly Arg Gly Ile Asn Val Ala Leu Ala Asn Gly Lys
                100                 105                 110 aca gga gaa gta tta gac act aaa tat ttt ggc atg tgg gga gga gat    384
Thr Gly Glu Val Leu Asp Thr Lys Tyr Phe Gly Met Trp Gly Gly Asp
            115                 120                 125 gtg gca cca ttt att gag ttt ctg aag gcc ata caa gat gga aca ata    432
Val Ala Pro Phe Ile Glu Phe Leu Lys Ala Ile Gln Asp Gly Thr Ile
        130                 135                 140 gtt tta atg gga aca tac gat gat gga gca acc aaa ctc aat gat gag    480
Val Leu Met Gly Thr Tyr Asp Asp Gly Ala Thr Lys Leu Asn Asp Glu
145                 150                 155                 160
```

```
gca cgg cgg ctc att gct gat ttg ggg agc aca tct att act aat ctt    528
Ala Arg Arg Leu Ile Ala Asp Leu Gly Ser Thr Ser Ile Thr Asn Leu
            165                 170                 175 ggt ttt aga gac aac tgg gtc ttc tgt ggt ggg aag ggc att aag aca    576
Gly Phe Arg Asp Asn Trp Val Phe Cys Gly Gly Lys Gly Ile Lys Thr
        180                 185                 190 aaa agc cct ttt gaa cag cac ata aag aac aat aag gat aca aac aaa    624
Lys Ser Pro Phe Glu Gln His Ile Lys Asn Asn Lys Asp Thr Asn Lys
    195                 200                 205 tat gaa gga tgg cct gaa gtt gta gaa atg gaa gga tgc atc ccc cag    672
Tyr Glu Gly Trp Pro Glu Val Val Glu Met Glu Gly Cys Ile Pro Gln
210                 215                 220 aag caa gac taa                                                    684
Lys Gln Asp *
225

<210> SEQ ID NO 6
<211> LENGTH: 227
<212> TYPE: PRT
<213> ORGANISM: Homo Sapiens

<400> SEQUENCE: 6

Met Arg Val Ala Gly Ala Ala Lys Leu Val Val Ala Val Ala Val Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
            85                  90                  95

Lys Asn Asn Val Gly Arg Gly Ile Asn Val Ala Leu Ala Asn Gly Lys
        100                 105                 110

Thr Gly Glu Val Leu Asp Thr Lys Tyr Phe Gly Met Trp Gly Gly Asp
    115                 120                 125

Val Ala Pro Phe Ile Glu Phe Leu Lys Ala Ile Gln Asp Gly Thr Ile
130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
            165                 170                 175

Gly Phe Arg Asp Asn Trp Val Phe Cys Gly Gly Lys Gly Ile Lys Thr
        180                 185                 190

Lys Ser Pro Phe Glu Gln His Ile Lys Asn Asn Lys Asp Thr Asn Lys
    195                 200                 205

Tyr Glu Gly Trp Pro Glu Val Val Glu Met Glu Gly Cys Ile Pro Gln
210                 215                 220

Lys Gln Asp
225

<210> SEQ ID NO 7
<211> LENGTH: 684
<212> TYPE: DNA
<213> ORGANISM: Homo Sapiens
<220> FEATURE:
```

```
<221> NAME/KEY: CDS
<222> LOCATION: (1)...(684)

<400> SEQUENCE: 7 atg agg gta gca ggt gct gca aag ttg gtg gta gct gtg gca gtg ttt      48
Met Arg Val Ala Gly Ala Ala Lys Leu Val Val Ala Val Ala Val Phe
 1               5                  10                  15 tta ctg aca ttt tat gtt att tct caa gta ttt gaa ata aaa atg gat      96
Leu Leu Thr Phe Tyr Val Ile Ser Gln Val Phe Glu Ile Lys Met Asp
             20                  25                  30 gca agt tta gga aat cta ttt gca aga tca gca ttg gac aca gct gca     144
Ala Ser Leu Gly Asn Leu Phe Ala Arg Ser Ala Leu Asp Thr Ala Ala
         35                  40                  45 cgt tct aca aag cct ccc aga tat aag tgt ggg atc tca aaa gct tgc     192
Arg Ser Thr Lys Pro Pro Arg Tyr Lys Cys Gly Ile Ser Lys Ala Cys
     50                  55                  60 cct gag aag cat ttt gct ttt aaa atg gca agt gga gca gcc aac gtg     240
Pro Glu Lys His Phe Ala Phe Lys Met Ala Ser Gly Ala Ala Asn Val
 65                  70                  75                  80 gtg gga ccc aaa atc tgc ctg gaa gat aat gtt tta atg agt ggt gtt     288
Val Gly Pro Lys Ile Cys Leu Glu Asp Asn Val Leu Met Ser Gly Val
                 85                  90                  95 aag aat aat gtt gga aga ggg atc aat gtt gcc ttg gca aat gga aaa     336
Lys Asn Asn Val Gly Arg Gly Ile Asn Val Ala Leu Ala Asn Gly Lys
            100                 105                 110 aca gga gaa gta tta gac act aaa tat ttt gac atg tgg gga gga gat     384
Thr Gly Glu Val Leu Asp Thr Lys Tyr Phe Asp Met Trp Gly Gly Asp
        115                 120                 125 gcg gca cca ttt att gag ttt ctg aag gcc ata caa gat gga aca ata     432
Ala Ala Pro Phe Ile Glu Phe Leu Lys Ala Ile Gln Asp Gly Thr Ile
    130                 135                 140 gtt tta atg gga aca tac gat gat gga gca acc aaa ctc aat gat gag     480
Val Leu Met Gly Thr Tyr Asp Asp Gly Ala Thr Lys Leu Asn Asp Glu
145                 150                 155                 160 gca cgg cgg ctc att gct gat ttg ggg agc aca tct att act aat ctt     528
Ala Arg Arg Leu Ile Ala Asp Leu Gly Ser Thr Ser Ile Thr Asn Leu
                165                 170                 175 ggt ttt aga gac aac tgg gtc ttc tgt ggt ggg aag ggc att aag aca     576
Gly Phe Arg Asp Asn Trp Val Phe Cys Gly Gly Lys Gly Ile Lys Thr
            180                 185                 190 aaa agc cct ttt gaa cag cac ata aag aac aat aag gat aca aac aaa     624
Lys Ser Pro Phe Glu Gln His Ile Lys Asn Asn Lys Asp Thr Asn Lys
        195                 200                 205 tat gaa gga tgg cct gaa gtt gta gaa atg gaa gga tgc atc ccc cag     672
Tyr Glu Gly Trp Pro Glu Val Val Glu Met Glu Gly Cys Ile Pro Gln
    210                 215                 220 aag caa gac taa                                                     684
Lys Gln Asp *
225

<210> SEQ ID NO 8
<211> LENGTH: 227
<212> TYPE: PRT
<213> ORGANISM: Homo Sapiens

<400> SEQUENCE: 8

Met Arg Val Ala Gly Ala Ala Lys Leu Val Val Ala Val Ala Val Phe
 1               5                  10                  15

Leu Leu Thr Phe Tyr Val Ile Ser Gln Val Phe Glu Ile Lys Met Asp
             20                  25                  30
```

```
Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Met Trp Gly Gly Asp
        115                 120                 125

Ala Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Lys Gly Ile Lys Thr
            180                 185                 190

Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
    210                 215                 220

Lys Gln Asp
225

<210> SEQ ID NO 9
<211> LENGTH: 684
<212> TYPE: DNA
<213> ORGANISM: Homo Sapiens
<220> FEATURE:
<221> NAME/KEY: CDS
<222> LOCATION: (1)...(684)

<400> SEQUENCE: 9 atg agg gta gca ggt gct gca aag ttg gtg gta gct gtg gca gtg ttt     48
Met Arg Val Ala Gly Ala Ala Lys Leu Val Val Ala Val Ala Val Phe
1               5                   10                  15 tta ctg aca ttt tat gtt att tct caa gta ttt gaa ata aaa atg gat    96
Leu Leu Thr Phe Tyr Val Ile Ser Gln Val Phe Glu Ile Lys Met Asp
            20                  25                  30 gca agt tta gga aat cta ttt gca aga tca gca ttg gac aca gct gca   144
Ala Ser Leu Gly Asn Leu Phe Ala Arg Ser Ala Leu Asp Thr Ala Ala
        35                  40                  45 cgt tct aca aag cct ccc aga tat aag tgt ggg atc tca aaa gct tgc   192
Arg Ser Thr Lys Pro Pro Arg Tyr Lys Cys Gly Ile Ser Lys Ala Cys
    50                  55                  60 cct gag aag cat ttt gct ttt aaa atg gca agt gga gca gcc aac gtg   240
Pro Glu Lys His Phe Ala Phe Lys Met Ala Ser Gly Ala Ala Asn Val
65                  70                  75                  80 gtg gga ccc aaa atc tgc ctg gaa gat aat gtt tta atg agt ggt gtt   288
Val Gly Pro Lys Ile Cys Leu Glu Asp Asn Val Leu Met Ser Gly Val
                85                  90                  95 aag aat aat gtt gga aga ggg atc aat gtt gcc ttg gca aat gga aaa   336
Lys Asn Asn Val Gly Arg Gly Ile Asn Val Ala Leu Ala Asn Gly Lys
            100                 105                 110 aca gga gaa gta tta gac act aaa tat ttt gac atg tgg gga gga gat   384
```

```
                                                                            -continued Thr Gly Glu Val Leu Asp Thr Lys Tyr Phe Asp Met Trp Gly Gly Asp
            115                 120                 125 gtg gca cca ctt att gag ttt ctg aag gcc ata caa gat gga aca ata       432
Val Ala Pro Leu Ile Glu Phe Leu Lys Ala Ile Gln Asp Gly Thr Ile
    130                 135                 140 gtt tta atg gga aca tac gat gat gga gca acc aaa ctc aat gat gag       480
Val Leu Met Gly Thr Tyr Asp Asp Gly Ala Thr Lys Leu Asn Asp Glu
145                 150                 155                 160 gca cgg cgg ctc att gct gat ttg ggg agc aca tct att act aat ctt       528
Ala Arg Arg Leu Ile Ala Asp Leu Gly Ser Thr Ser Ile Thr Asn Leu
                165                 170                 175 ggt ttt aga gac aac tgg gtc ttc tgt ggt ggg aag ggc att aag aca       576
Gly Phe Arg Asp Asn Trp Val Phe Cys Gly Gly Lys Gly Ile Lys Thr
            180                 185                 190 aaa agc cct ttt gaa cag cac ata aag aac aat aag gat aca aac aaa       624
Lys Ser Pro Phe Glu Gln His Ile Lys Asn Asn Lys Asp Thr Asn Lys
        195                 200                 205 tat gaa gga tgg cct gaa gtt gta gaa atg gaa gga tgc atc ccc cag       672
Tyr Glu Gly Trp Pro Glu Val Val Glu Met Glu Gly Cys Ile Pro Gln
    210                 215                 220 aag caa gac taa                                                        684
Lys Gln Asp *
225

<210> SEQ ID NO 10
<211> LENGTH: 227
<212> TYPE: PRT
<213> ORGANISM: Homo Sapiens

<400> SEQUENCE: 10

Met Arg Val Ala Gly Ala Ala Lys Leu Val Ala Val Ala Val Phe
  1               5                  10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Met Trp Gly Gly Asp
        115                 120                 125

Val Ala Pro Leu Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
```

```
                       210                 215                 220
Lys Gln Asp
225

<210> SEQ ID NO 11
<211> LENGTH: 684
<212> TYPE: DNA
<213> ORGANISM: Homo Sapiens
<220> FEATURE:
<221> NAME/KEY: CDS
<222> LOCATION: (1)...(684)

<400> SEQUENCE: 11 atg agg gta gca ggt gct gca aag ttg gtg gta gct gtg gca gtg ttt        48
Met Arg Val Ala Gly Ala Ala Lys Leu Val Val Ala Val Ala Val Phe
 1               5                  10                  15 tta ctg aca ttt tat gtt att tct caa gta ttt gaa ata aaa atg gat        96
Leu Leu Thr Phe Tyr Val Ile Ser Gln Val Phe Glu Ile Lys Met Asp
             20                  25                  30 gca agt tta gga aat cta ttt gca aga tca gca ttg gac aca gct gca       144
Ala Ser Leu Gly Asn Leu Phe Ala Arg Ser Ala Leu Asp Thr Ala Ala
         35                  40                  45 cgt tct aca aag cct ccc aga tat aag tgt ggg atc tca aaa gct tgc       192
Arg Ser Thr Lys Pro Pro Arg Tyr Lys Cys Gly Ile Ser Lys Ala Cys
     50                  55                  60 cct gag aag cat ttt gct ttt aaa atg gca agt gga gca gcc aac gtg       240
Pro Glu Lys His Phe Ala Phe Lys Met Ala Ser Gly Ala Ala Asn Val
 65                  70                  75                  80 gtg gga ccc aaa atc tgc ctg gaa gat gat gtt tta atg agt ggt gtt       288
Val Gly Pro Lys Ile Cys Leu Glu Asp Asp Val Leu Met Ser Gly Val
                 85                  90                  95 aag aat aat gtt gga aga ggg atc aat gtt gcc ttg gca aat gga aaa       336
Lys Asn Asn Val Gly Arg Gly Ile Asn Val Ala Leu Ala Asn Gly Lys
            100                 105                 110 aca gga gaa gta tta gac act aaa tat ttt gac atg tgg gga gga gat       384
Thr Gly Glu Val Leu Asp Thr Lys Tyr Phe Asp Met Trp Gly Gly Asp
        115                 120                 125 gcg gca cca ttt att gag ttt ctg aag gcc ata cag gat gga aca ata       432
Ala Ala Pro Phe Ile Glu Phe Leu Lys Ala Ile Gln Asp Gly Thr Ile
    130                 135                 140 gtt tta atg gga aca tac gat gat gga gca acc aaa ctc aat gat gag       480
Val Leu Met Gly Thr Tyr Asp Asp Gly Ala Thr Lys Leu Asn Asp Glu
145                 150                 155                 160 gca cgg cgg ctc att gct gat ttg ggg agc aca tct att act aat ctt       528
Ala Arg Arg Leu Ile Ala Asp Leu Gly Ser Thr Ser Ile Thr Asn Leu
                165                 170                 175 ggt ttt aga gac aac tgg gtc ttc tgt ggt ggg aag ggc att aag aca       576
Gly Phe Arg Asp Asn Trp Val Phe Cys Gly Gly Lys Gly Ile Lys Thr
            180                 185                 190 aaa agc cct ttt gaa cag cac ata aag aac aat aag gat aca aac aaa       624
Lys Ser Pro Phe Glu Gln His Ile Lys Asn Asn Lys Asp Thr Asn Lys
        195                 200                 205 tat gaa gga tgg cct gaa gtt gta gaa atg gaa gga tgc atc ccc cag       672
Tyr Glu Gly Trp Pro Glu Val Val Glu Met Glu Gly Cys Ile Pro Gln
    210                 215                 220 aag caa gac taa                                                       684
Lys Gln Asp *
225

<210> SEQ ID NO 12
<211> LENGTH: 227
```

```
<212> TYPE: PRT
<213> ORGANISM: Homo Sapiens

<400> SEQUENCE: 12

Met Arg Val Ala Gly Ala Ala Lys Leu Val Val Ala Val Ala Val Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asp Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Met Trp Gly Gly Asp
        115                 120                 125

Ala Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
    210                 215                 220

Lys Gln Asp
225

<210> SEQ ID NO 13
<211> LENGTH: 684
<212> TYPE: DNA
<213> ORGANISM: Homo Sapiens
<220> FEATURE:
<221> NAME/KEY: CDS
<222> LOCATION: (1)...(684)

<400> SEQUENCE: 13 atg agg gta gca ggt gct gca aag ttg gtg gta gct gtg gca gcg ttt    48
Met Arg Val Ala Gly Ala Ala Lys Leu Val Val Ala Val Ala Val Phe
1               5                   10                  15 tta ctg aca ttt tat gtt att tct caa gta ttt gaa ata aaa atg gat   96
Leu Leu Thr Phe Tyr Val Ile Ser Gln Val Phe Glu Ile Lys Met Asp
            20                  25                  30 gca agt tta gga aat cta ttt gca aga tca gca ttg gac aca gct gca   144
Ala Ser Leu Gly Asn Leu Phe Ala Arg Ser Ala Leu Asp Thr Ala Ala
        35                  40                  45 cgt tct aca aag cct ccc aga tat aag tgt ggg atc tca aaa gct tgc   192
Arg Ser Thr Lys Pro Pro Arg Tyr Lys Cys Gly Ile Ser Lys Ala Cys
50                  55                  60 cct gag aag cat ttt gct ttt aaa atg gca agt gga gca gcc aac gtg   240
Pro Glu Lys His Phe Ala Phe Lys Met Ala Ser Gly Ala Ala Asn Val
```

-continued

```
                65                  70                  75                  80
gtg gga ccc aaa atc tgc ctg gaa gat aat gtt tta atg agt ggt gtt        288
Val Gly Pro Lys Ile Cys Leu Glu Asp Asn Val Leu Met Ser Gly Val
                    85                  90                  95 aag aat aat gtt gga aga ggg atc aat gtt gcc ttg gca aat gga aaa        336
Lys Asn Asn Val Gly Arg Gly Ile Asn Val Ala Leu Ala Asn Gly Lys
                100                 105                 110 aca gga gaa gta tta gac act aaa tat ttt ggc atg tgg gga gga gat        384
Thr Gly Glu Val Leu Asp Thr Lys Tyr Phe Gly Met Trp Gly Gly Asp
            115                 120                 125 gtg gca cca ttt att gag ttt ctg aag gcc ata caa gat gga aca ata        432
Val Ala Pro Phe Ile Glu Phe Leu Lys Ala Ile Gln Asp Gly Thr Ile
        130                 135                 140 gtt tta atg gga aca tac gat gat gga gca acc aaa ctc aat gat gag        480
Val Leu Met Gly Thr Tyr Asp Asp Gly Ala Thr Lys Leu Asn Asp Glu
145                 150                 155                 160 gca cgg cgg ctc att gct gat ttg ggg agc aca tct att act aat ctt        528
Ala Arg Arg Leu Ile Ala Asp Leu Gly Ser Thr Ser Ile Thr Asn Leu
                165                 170                 175 ggt ttt aga gac aac tgg gtc ttc tgt ggt ggg aag ggc att aag aca        576
Gly Phe Arg Asp Asn Trp Val Phe Cys Gly Gly Lys Gly Ile Lys Thr
                180                 185                 190 aaa agc cct ttt gaa cag cac ata aag aac aat aag gat aca aac aaa        624
Lys Ser Pro Phe Glu Gln His Ile Lys Asn Asn Lys Asp Thr Asn Lys
            195                 200                 205 tat gaa gga tgg cct gaa gtt gta gaa atg gaa gga tgc atc ccc cag        672
Tyr Glu Gly Trp Pro Glu Val Val Glu Met Glu Gly Cys Ile Pro Gln
        210                 215                 220 aag caa gac taa                                                         684
Lys Gln Asp *
225

<210> SEQ ID NO 14
<211> LENGTH: 227
<212> TYPE: PRT
<213> ORGANISM: Homo Sapiens

<400> SEQUENCE: 14

Met Arg Val Ala Gly Ala Ala Lys Leu Val Val Ala Val Ala Ala Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Gly Met Trp Gly Gly Asp
        115                 120                 125

Val Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160
```

```
Ala Arg Arg Leu Ile Ala Asp Leu Gly Ser Thr Ser Ile Thr Asn Leu
            165                 170                 175

Gly Phe Arg Asp Asn Trp Val Phe Cys Gly Gly Lys Gly Ile Lys Thr
        180                 185                 190

Lys Ser Pro Phe Glu Gln His Ile Lys Asn Asn Lys Asp Thr Asn Lys
    195                 200                 205

Tyr Glu Gly Trp Pro Val Val Glu Met Gly Cys Ile Pro Gln
210                 215                 220

Lys Gln Asp
225

<210> SEQ ID NO 15
<211> LENGTH: 684
<212> TYPE: DNA
<213> ORGANISM: Homo Sapiens
<220> FEATURE:
<221> NAME/KEY: CDS
<222> LOCATION: (1)...(684)

<400> SEQUENCE: 15 atg agg gta gca ggt gct gca aag ttg gtg gta gct gtg gca gtg ttt        48
Met Arg Val Ala Gly Ala Ala Lys Leu Val Val Ala Val Ala Val Phe
 1               5                  10                  15 tta ctg aca ttt tat gtt att tct caa gta ttt gaa ata aaa atg gat        96
Leu Leu Thr Phe Tyr Val Ile Ser Gln Val Phe Glu Ile Lys Met Asp
             20                  25                  30 gca agt tta gga aat cta ttt gca aga tca gct ttg gac aca gct gca       144
Ala Ser Leu Gly Asn Leu Phe Ala Arg Ser Ala Leu Asp Thr Ala Ala
         35                  40                  45 cgt tct aca aag cct ccc aga tat aag tgt ggg atc tca aaa gct tgc       192
Arg Ser Thr Lys Pro Pro Arg Tyr Lys Cys Gly Ile Ser Lys Ala Cys
     50                  55                  60 cct gag aag cat ttt gct ttt aaa atg gca agt gga gca gcc aac gtg       240
Pro Glu Lys His Phe Ala Phe Lys Met Ala Ser Gly Ala Ala Asn Val
 65                  70                  75                  80 gtg gga ccc aaa atc tgc ctg gaa gat aat gtt tta atg agt ggt gtt       288
Val Gly Pro Lys Ile Cys Leu Glu Asp Asn Val Leu Met Ser Gly Val
                 85                  90                  95 aag aat aat gtt gga aga ggg atc aat gtt gcc ttg gca aat gga aaa       336
Lys Asn Asn Val Gly Arg Gly Ile Asn Val Ala Leu Ala Asn Gly Lys
            100                 105                 110 aca gga gaa gta tta gac act aaa tat ttt gac ctg tgg gga gga gat       384
Thr Gly Glu Val Leu Asp Thr Lys Tyr Phe Asp Leu Trp Gly Gly Asp
        115                 120                 125 gtg gca cca ttt att gag ttt ctg aag gcc ata caa gat gga aca ata       432
Val Ala Pro Phe Ile Glu Phe Leu Lys Ala Ile Gln Asp Gly Thr Ile
    130                 135                 140 gtt tta atg gga aca tac gat gat gga gca acc aaa ctc aat gat gag       480
Val Leu Met Gly Thr Tyr Asp Asp Gly Ala Thr Lys Leu Asn Asp Glu
145                 150                 155                 160 gca cgg cgg ctc att gct gat ttg ggg agc aca tct att act aat ctt       528
Ala Arg Arg Leu Ile Ala Asp Leu Gly Ser Thr Ser Ile Thr Asn Leu
                165                 170                 175 ggt ttt aga gac aac tgg gtc ttc tgt ggt ggg aag ggc att aag aca       576
Gly Phe Arg Asp Asn Trp Val Phe Cys Gly Gly Lys Gly Ile Lys Thr
            180                 185                 190 aaa agc ccc ttt gaa cag cac ata aag aac aat aag gat aca aac aaa       624
Lys Ser Pro Phe Glu Gln His Ile Lys Asn Asn Lys Asp Thr Asn Lys
        195                 200                 205
```

```
                                                                                              -continued
tat gaa gga tgg cct gaa gtt gta gaa atg gaa gga tgc atc ccc cag                          672
Tyr Glu Gly Trp Pro Glu Val Val Glu Met Glu Gly Cys Ile Pro Gln
    210                 215                 220 aag caa gac taa                                                                          684
Lys Gln Asp *
225

<210> SEQ ID NO 16
<211> LENGTH: 227
<212> TYPE: PRT
<213> ORGANISM: Homo Sapiens

<400> SEQUENCE: 16

Met Arg Val Ala Gly Ala Ala Lys Leu Val Ala Val Ala Val Phe
1               5                   10                  15

Leu Leu Thr Phe Tyr Val Ile Ser Gln Val Phe Glu Ile Lys Met Asp
                20                  25                  30

Ala Ser Leu Gly Asn Leu Phe Ala Arg Ser Ala Leu Asp Thr Ala Ala
            35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Leu Trp Gly Gly Asp
        115                 120                 125

Val Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
    210                 215                 220

Lys Gln Asp
225
```